(12) United States Patent
Becker (10) Patent No.: US 7,888,127 B2
(45) Date of Patent: Feb. 15, 2011

(54) METHODS FOR REDUCING ADDUCT FORMATION FOR MASS SPECTROMETRY ANALYSIS

(75) Inventor: Thomas Becker, La Jolla, CA (US)

(73) Assignee: Sequenom, Inc., San Diego, CA (US)

(*) Notice: Subject to any disclaimer, the term of this patent is extended or adjusted under 35 U.S.C. 154(b) by 0 days.

(21) Appl. No.: 12/014,671

(22) Filed: Jan. 15, 2008

(65) Prior Publication Data

US 2009/0181376 A1 Jul. 16, 2009

(51) Int. Cl.
*G01N 33/00* (2006.01)
*G01N 24/00* (2006.01)
*G01N 1/00* (2006.01)
*C07H 21/04* (2006.01)

(52) U.S. Cl. .................. 436/94; 436/173; 436/175; 536/23.1

(58) Field of Classification Search .................. None
See application file for complete search history.

(56) References Cited

U.S. PATENT DOCUMENTS

| 6,468,748 | B1 | 10/2002 | Monforte et al. | |
|---|---|---|---|---|
| 6,723,564 | B2 | 4/2004 | Hillenkamp | |
| 2005/0074759 | A1* | 4/2005 | Petersson et al. | 435/6 |
| 2007/0298006 | A1* | 12/2007 | Tomalia et al. | 424/78.03 |

FOREIGN PATENT DOCUMENTS

| WO | WO 97/27325 | 7/1997 |
|---|---|---|
| WO | WO 99/05319 | 2/1999 |
| WO | WO 2009/091841 | 10/2009 |

OTHER PUBLICATIONS

Djoman et al., "RNA-ascorbate interaction," Journal of Biomolecular Structure and Dynamics, Jun. 1998, vol. 15, No. 6, pp. 1115-1120. Abstract only.*
Neault et al., "DNA-drug interaction. The effects of vitamin C on the solution structure of calf thymus DNA studied by FTIR and laser Raman difference spectroscopy," Journal of Biomolecular Structure and Dynamics, 1995, vol. 13, No. 2, pp. 387-397. Abstract o n ly.*
International Search Report and Written Opinion, mailed on: Aug. 19, 2009 for International application No.: PCT/US2009/031020 filed on Jan. 12, 2009 and published as WO 09/091841 on: Oct. 8, 2009.
Asara and Alison, "Enhanced Detection of Oligonucleotides in UV MALDI MS Using the Tetraamine Spermine as a Matrix Additive," Anal Chem, 1999, 71, 2866-2870.
Chen and Chen, "Reducing the Alkali Cation Adductions of oligonucleotides Using Sol-Gel-Assisted Laser Desorption/Ionization Mass Spectometry," Anal, Chem., 75, 4223-4228 (2003).
Electrospray Ionization Mass Spectrometry: Fundamentals, Instrumentation and Applications edited by Cole (John Wiley and Sons, New York), (1997).

(Continued)

*Primary Examiner*—Bradley L Sisson
(74) *Attorney, Agent, or Firm*—Grant Anderson LLP (57) ABSTRACT

The invention provides a novel additive for improved analysis by mass spectrometry. More specifically, ascorbic acid has been found to reduce or eliminate the presence of adducts commonly present in mass spectra. The improved processes and compositions of the invention allow for increased accuracy, sensitivity and throughput for samples analyzed by mass spectrometry.

14 Claims, 4 Drawing Sheets

OTHER PUBLICATIONS

Jurinke, C., Oeth, P., van den Boom, D., "MALDI-TOF mass spectrometry: a versatile tool for high-performance DNA analysis", Mol. Biotechnol. 26, 147-164 (2004).

Laugesen and Roepstroff, "Combination of Two Matricies Results in Improved Performance of MALDI MS for Peptide Mass Mapping and Protein Analysis," J. Am. Soc. Mass Spectrom, 2003, 14, 992-1002.

Li et al. "Evaluation of ammonium salts as co-matrices for matrix-assisted laser desorption/ionization mass spectrometry of oligonucleotides" Rapid Comm. Mass Spectrom. 12:993-998 (1998).

M.C. Fitzgerald and L.M. Smith, Annu. Rev. Biophys. Biomol. Struc. 1995. 24:117-140.

Nordhoff et al., "Mass spectrometry of nucleic acids" Mass Spectrometry Reviews, 1996, 15, 67-138.

Nordhoff, E., et al., "Matrix-assisted Laser Desorption/Ionization Mass Spectrometry of Nucleic Acids with Wavelengths in the Ultraviolet and Infrared" Rapid Comm. Mass Spectrom. 1992, 6, 771-776.

Oeth, P. et al., "iPLEX™ Assay: Increased Plexing Efficiency and Flexibility for MassARRAY® System through single base primer extension with mass-modified Terminators" SEQUENOM Application Note (2005).

Pieles, et al., "Matrix-assisted laser desorption ionization time-of-flight mass spectrometry: a powerful tool for the mass and sequence analysis of natural and modified oligonucleotides," Nucleic Acid Research, 1993, 21:14, 3191-3196.

Shahgoli et al, "Sugar additives for MALDI matrices improve signal allowing the smallest nucleotide change (A:T) in a DNA sequence to be resolved," Nucleic Acids Research 2001, 21:19, e91 1-10.

Wu, J.K., et al., "Matrix-assisted Laser Desorption Time-of-flight Mass Spectrometry of Oligonucleotides Using 3-Hydroxypicolinic Acid as an Ultraviolet-sensitive Matrix," Rapid Comm. Mass Spectrom. 1993, 7:142-146.

Zenobi et al., "Ion Formation in MALDI Mass Spectrometry," Mass Spectrometry Reviews. 1998, 17, 341.

Zhou et al., "A mixed matrix of 3-hydroxypicolinic acid and pyrazinercarboxylic acid for matrix-assisted laser desorption/ionization time-of-flight mass spectrometry of oligodeoxynucleotides," Rapid Communications in Mass Spectrometry, 2003:18:787-794.

International Preliminary Report on Patentability, mailed on: Jul. 29, 2010 for International application No.: PCT/US2009/031020 filed on Jan. 12, 2009 and published as WO 09/091841 on: Oct. 8, 2009.

* cited by examiner

METHODS FOR REDUCING ADDUCT FORMATION FOR MASS SPECTROMETRY ANALYSIS

FIELD OF THE INVENTION

The invention pertains generally to compositions and methods for use with mass spectrometry.

BACKGROUND

Mass spectrometry is a powerful analytical tool used for measuring the molecular mass of analytes in a sample. When using a time-of-flight mass spectrometer, the speed of flight of the ions is about $10^7$ times faster than the speed of migration of molecules in an electrophoretic gel, therefore mass spectrometry offers an extremely fast analytical method, even when measurement of the spectrum is repeated 10 to 100 times to achieve a good signal-to-noise ratio.

Analysis by mass spectrometry typically begins with the samples being ionized by any number of means, for example, by Matrix Assisted Laser Desorption Ionization (MALDI) or Electrospray Ionization (ES). MALDI preparation and measurement procedures consist first of embedding the analyte molecules on a sample carrier in a solid, IR or UV-absorbent matrix which is usually an organic acid. The sample carrier comprising the matrix and analyte is placed in the ion source of a mass spectrometer. The matrix is vaporized by a short laser pulse and the analyte molecule is thereby transported into the gas phase in a non-fragmented state. The analyte molecule is ionized by colliding and reacting with the matrix ions generated at the same time. A voltage is applied which accelerates the ions into a field-free flight tube. Due to their different masses, the ions in the ion source are accelerated to different speeds with the smaller ions reaching the detector earlier than the larger ions. The varying times of flight are converted into the different masses of the ions.

An alternative method for ionizing an analyte is electrospray (or ES). Like MALDI, electrospray allows for the ionization/vaporization of polar molecules. Initially the sample of interest is dissolved in a solvent where, to a certain extent, it will exist in an ionized form. In conventional ES, the solution is then pumped through a thin capillary which is raised to a high potential. Small charged droplets are sprayed from the ES capillary into a bath gas at atmospheric pressure and travel down a pressure and potential gradient towards an orifice in the mass-spectrometer high-vacuum system. As the droplets traverse this path, they become desolvated and reduced in size such that surface-Coulombic forces overcome surface-tension forces. As a result, the droplets break up into smaller droplets until either an ion desorbs from the droplet or the solvent is completely removed. The exact mechanism of ion formation is not entirely clear, but the result is a beam of ions, which are sampled by the mass spectrometer. A more detailed description of the ES process is provided in *Electrospray Ionization Mass Spectrometry: Fundamentals, Instrumentation and Applications* edited by Cole (John Wiley and Sons, New York).

Whichever ionization method used, the formation of unwanted adducts during ionization can compromise the quality and resolution of spectra generated by mass spectrometry. More specifically, the presence of unwanted adducts can make it difficult to detect and analyze an analyte, especially low abundance or low mass analytes.

SUMMARY

The present invention provides processes and compositions for improved analysis by mass spectrometry. Provided herein are mass spectrometric sample preparation methods that reduce or minimize adduct formation in a cost effective and easy-to-implement manner that does not otherwise disrupt the ionization, mass analysis or detection of sample ions. The improved methods and compositions of the invention allow for easier identification and quantification of analyte peaks, thereby increasing the number of correct calls. These improvements prove particularly useful for samples contaminated with sodium and/or ammonia salt, as well as samples with low analyte concentrations. In certain embodiments, described hereafter is the use of ascorbic acid, or a salt, tautomer or analog thereof, as an adduct-reducing additive that decreases the presence of adducts in the mass spectra, and increases the signal to noise (s/n) ratio. While embodiments of the invention will refer to using "ascorbic acid" hereafter, it is understood that the person of ordinary skill in the art can use ascorbic acid, ascorbate, a salt thereof, a tautomer thereof or an analog thereof (described hereafter) in methods and compositions described herein.

In one aspect, the invention provides a method for reducing adduct formation in a sample comprising an analyte to be analyzed by mass spectrometry comprising the step of adding an adduct-reducing additive, which comprises ascorbic acid, to the sample prior to analysis of the analyte by mass spectrometry. In a related embodiment, the adduct-reducing additive may further comprise ammonium oxalate. In some embodiments, the adduct-reducing additive is used in combination with other adduct-reducing additives (known or not-yet-discovered adduct-reducing additives). In certain embodiments, the adduct-reducing additive is used in combination with one or more resins.

In certain embodiments, the analyte is a nucleic acid such as deoxyribonucleic acid or ribonucleic acid. Improvements described herein can be applied to a variety of mass spectrometry formats as sample handling procedures prior to mass analysis can generate undesirable adducts. Examples of mass spectrometry formats include, but are not limited to, Matrix-Assisted Laser Desorption/Ionization Time-of-Flight (MALDI-TOF) Mass Spectrometry (MS), Laser Desorption Mass Spectrometry (LDMS), Electrospray (ES) MS, Ion Cyclotron Resonance (ICR) MS, and Fourier Transform MS. Improvements described herein are readily applicable to mass spectrometry formats in which analyte is volatized and ionized ("ionization MS," e.g., MALDI-TOF MS, LDMS, ESMS).

The invention also provides a method for reducing adduct formation in a sample comprising an analyte to be analyzed by mass spectrometry comprising the step of adding an adduct-reducing additive, which comprises ascorbic acid, to a matrix prior to analysis of the analyte by mass spectrometry. The method may also comprise the additional step of adding the adduct-reducing additive to the analyte (as well as the matrix) prior to analysis of the analyte by mass spectrometry In a related embodiment, the adduct-reducing additive may further comprise ammonium oxalate. In some embodiments, the matrix composition comprises 3-hydroxypicolinic acid (3-HPA), di-ammonium citrate (DAC), or a combination thereof. In certain embodiments, the analyte is a nucleic acid such as deoxyribonucleic acid or ribonucleic acid. In some embodiments, the adduct-reducing additive is also added to the analyte.

In certain embodiments, the invention provides methods for preparing a substrate suitable for use in mass spectrometry comprising the step of depositing a matrix material comprising an adduct-reducing additive on the substrate, wherein the adduct-reducing additive comprises ascorbic acid. In a related embodiment, the adduct-reducing additive may further comprise ammonium oxalate. In another related embodiment, the method further comprises the step of sealing the substrate. Methods of sealing a substrate include, but are not limited to, conditions effected by packaging processes, such as vacuum sealing and heat sealing, for example. In some embodiments, the method further comprises the step of treating the substrate with an agent or gas to minimize oxidation. In certain embodiments, the substrate is flushed with an inert gas, for example argon, prior to being sealed. In certain embodiments, the substrate is sealed and/or packaged to limit or eliminate exposure to light or UV radiation prior to analysis by mass spectrometry. In some embodiments, the substrate is sealed and/or packaged to maintain a given pH. In certain embodiments, substrates are packaged in a container, including without limitation, a polymer container (e.g., polyethylene, polypropylene, polystyrene container). In some embodiments, the substrate comprises silica or silicon dioxide.

The invention also provides compositions to be analyzed by mass spectrometry comprising an analyte and an adduct-reducing additive. In certain embodiments, the adduct-reducing additive comprises ascorbic acid. In a related embodiment, the adduct-reducing additive may further comprise ammonium oxalate.

In some embodiments, the invention provides a composition suitable for analysis by mass spectrometry comprising an analyte and an adduct-reducing additive, wherein the additive comprises ascorbic acid. The composition may also comprise ammonium oxalate.

In certain embodiments, the invention provides a target site for mass spectrometry comprising a substrate and an adduct-reducing additive comprising ascorbic acid. The target site may also comprise ammonium oxalate. In some embodiments, the target site may further comprise a matrix material. In a related embodiment, the matrix material is pre-loaded on the substrate. In certain embodiments, the target site may further comprise an analyte. In some embodiments, the composition is sealed. Methods of sealing substrates include, but are not limited to, vacuum sealing and heat sealing. In certain embodiments, the composition is treated with an agent or gas to minimize oxidation. In some embodiments, the composition is flushed with an inert gas, for example argon, prior to being sealed. In some embodiments, the composition is sealed and/or packaged to limit or eliminate exposure to light or UV radiation. In certain embodiments, the composition is sealed and/or packaged to maintain a given pH.

Examples of mass spectrometry analysis that may be improved by the methods and compositions of the invention include, but are not limited to, nucleic acid sequencing, genotyping or methylation analysis. The analysis may be qualitative or quantitative analysis performed by mass spectrometry.

DETAILED DESCRIPTION

Mass spectrometry offers a highly accurate and sensitive way to measure the molecular mass of analytes such as nucleic acids and peptides. Mass spectrometry thereby provides a powerful tool for the analysis of otherwise difficult-to-measure molecules. However, the presence of unwanted adduct products can make it difficult to accurately detect and analyze an analyte, especially low abundance or low mass analytes. The problem is further compounded when multiple analytes are detected in a single mass spectrum as part of multiplexed reaction.

Adducts form when ions, typically cations, associate with biomolecules under mass spectrometry conditions, thereby creating unwanted mass peaks. Any part of the sample processing (e.g., biochemistry, sample handling, sample dispensing, etc), sample cleanup (e.g., adding resin) sample ionization, or sample detection may contribute to the formation of adducts.

Figure 1:
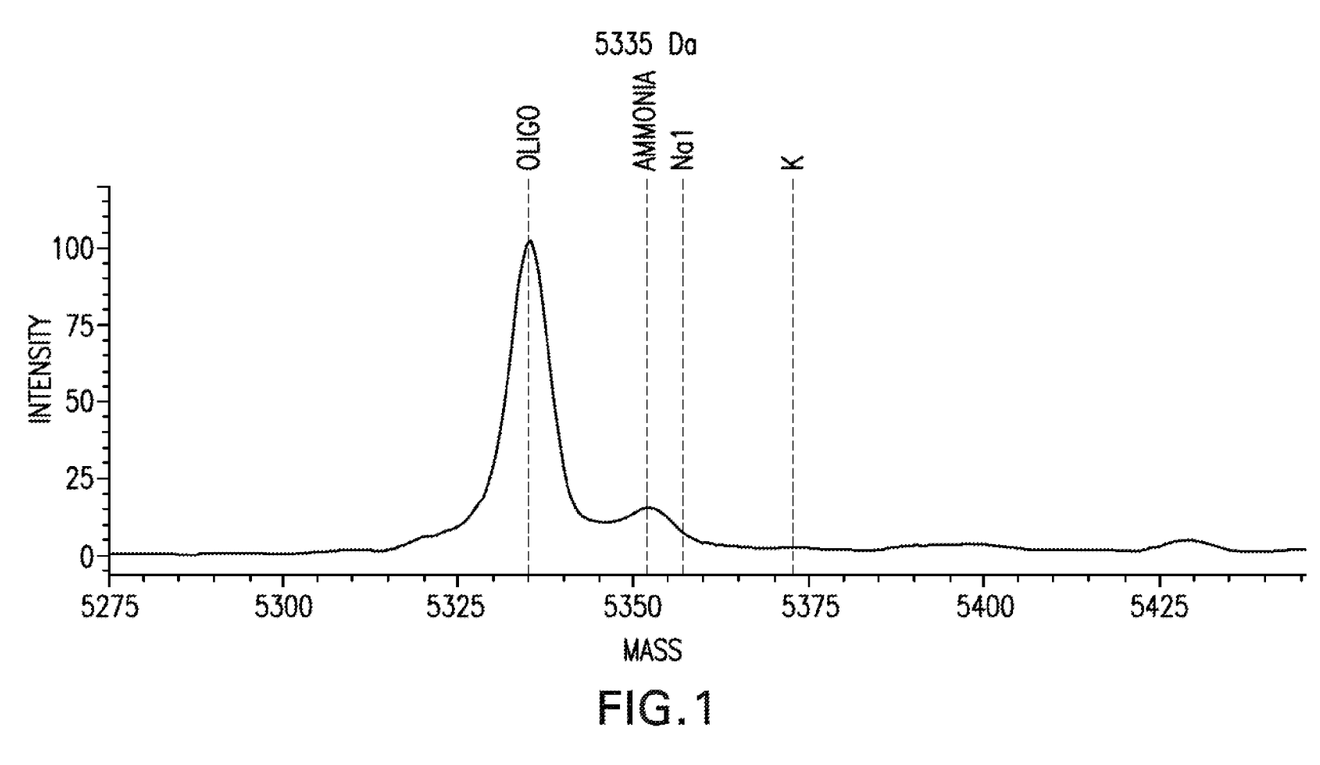
FIG. 1 shows a mass spectrum generated using a 17mer synthetic oligonucleotide (GTG GTG GTG GTG GTG GT (SEQ ID NO: 1)) spotted directly on the standard, unmodified matrix. In the Figure, the presence of an ammonia adduct is identified (peak height is approximately 12% of parent peak at 5335Da).

In the case of matrix-assisted laser desorption/ionization (MALDI) mass spectrometry, the matrix material itself may serve as a source of adduct formation. For example, a mixture of 3-hydroxypicolinic acid (3-HPA) and di-ammoniumcitrate (DAC) is often used as an effective UV-matrix for MALDI-based nucleic acid analysis. Ammonium salts (e.g., DAC) are added to matrices, and to 3-HPA in particular, because they are known to further reduce cation adduct formation to single-stranded DNA (ssDNA) (Wu, J. K., et al., *Rapid Comm. Mass Spectrom.* 1993, 7, 191; Pieles, et al., *Nucleic Acid Research*, 1993, 21, 14, 3191). However, results provided herein indicate DAC is the major source for ammonia ($NH_3$) adduct formation. For example, FIG. 1 shows the presence of an $NH_3$ adduct mass peak at +17 Da of the mass spectra.

Another contributor to ammonia adduct formation is ammoniated cation exchange resin, which may be used to desalt the analyte prior to MALDI analysis (Nordhoff, E., et al., *Rapid Comm. Mass Spectrom.* 1992, 6, 771). As described in the Examples below, ammonia adducts are predominantly formed with guanine and thymine bases. Thus, these adducts are more pronounced in assays where the nucleic acid analytes are rich in these bases.

In addition, ammoniated cation exchange resin may not completely remove all of the sodium ions from the DNA's backbone. This lack of removal results in a sodium ion adduct mass peak at +22 Da. Other adducts may form from the matrix material, and may be more common in the presence of thymine bases. For example, when 3-hydroxypicolinic acid is used as a matrix, adduct mass peaks are found at 94, 138, and 188

Da. Together, all of these adduct peaks can lead to a misinterpretation of mass spectrometry results. Thus compositions and processes that greatly reduce the amount and frequency of adducts, especially alkali and ammonia adducts, are useful for improving the accuracy, sensitivity and throughput of mass spectrometry-based analysis. Presence of an adduct-reducing additive can reduce, or abrogate, an adduct peak present for a sample analyzed without an adduct-reducing additive. As shown herein, the addition of ascorbic acid has been shown to reduce the average adduct formation score (defined herein) by up to 40% compared to resin-treated standard matrix at comparable extension product intensities (see Examples 1-3). In addition, matrix modified with ascorbic acid additive has proven to be physically and chemically stable over a period of 6 months (see Example 4) allowing for substrates to be pre-treated with ascorbic acid during manufacturing.

Analyte

The invention allows for improved mass spectrometry-based analysis of analytes such as nucleic acids, (e.g., oligonucleotides and polynucleotides), proteins, peptides and lipids, including their particular analogs and conjugates, such as glycoproteins or lipoproteins. Other substances that can be amenable to MALDI analysis within the present teachings are small molecules, metabolites, natural products and pharmaceuticals. The methods and compositions of the present invention are particularly useful for polynucleotides comprising a majority of guanines and thymines since these polynucleotides are more susceptible to ammonia adduct formation.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, acyclo nucleotides and other such analogs and derivatives or combinations thereof.

Nucleotide analogs contained in a polynucleotide can be, for example, mass modified nucleotides, which allow for mass differentiation of polynucleotides; nucleotides containing a detectable label such as a fluorescent, radioactive, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond, or the like, and is capable of being extended by a polymerase.

Sample

As used herein, "sample" refers to a composition containing an analyte to be analyzed. In certain embodiments, the sample is from a "biological sample". A biological material is generally considered any material obtained from a living source (e.g. human, animal, plant, bacteria, fungi, protist, virus)). The biological sample can be in any form, including solid materials (e.g. tissue, cell pellets and biopsies) and biological fluids (e.g. urine, blood, saliva, amniotic fluid and mouth wash (containing buccal cells)). Preferably solid materials are mixed with a fluid.

Matrix

Matrix material is utilized in certain forms of mass spectrometry, such as MALDI spectrometry, for example. The matrix material serves to separate the analyte molecules from each other, to absorb the energy imparted by the laser photons, and to transfer the energy to the analyte molecules, thereby resulting in their desorption and ionization. Once the analyte is ionized, a mass spectrometer such as a time of flight (TOF) analyzer can be used to measure ion masses.

The choice of a matrix material for mass spectrometry analysis often depends upon the type of biomolecules analyzed. For example, for nucleic acid analysis by mass spectrometry, a matrix often utilized is a mixture of 3-hydroxypicolinic acid (3-HPA) and di-ammoniumcitrate (DAC). Another matrix material used to facilitate ionization of sample analytes is 2,5-dihydroxybenzoic acid (DHB). DHB also suffers from adduct formation and chemical noise generation that interferes with sample analysis. Alpha-cyano-4-hydroxycinnamic acid ($\alpha$-CHCA) is an example of a widely used matrix for the ionization of protein and peptide analytes in matrix-assisted laser time-of-flight mass spectrometry. However, $\alpha$-CHCA adducts are common and can interfere with the ability to accurately detect low abundance, low mass analytes. Additional matrices that may be used with free radical scavenger additives described herein for the improved mass spectrometric analysis are described by Li et al. (*Rapid Comm. Mass Spectrom.* 12:993-998 (1998), M. C. Fitzgerald and L. M. Smith (Annu. Rev. Biophys. Biomol. Struc. 1995. 24: 117-40), and Nordhoff et al. (Mass Spectrometry Reviews, 1996, 15, 67-138; all of which are hereby incorporated by reference), and examples of matrices include, without limitation, 2,4,6-trihydroxyacetophenone (THAP), anthranilic acid, nicotinic acid, salicylamide, 1-isoquinolinol, T-2-(3-(4-t-Butyl-phenyl)-2-methyl-2-propenylidene) malononitrile (DCTB), sinapic acid (SA), dithranol (DIT), 3-aminoquinoline, trans-3-indoleacrylic acid (IAA), 2-(4-hydroxyphenylazo)benzoic acid (HABA), succinic acid, 2,6-dihydroxyacetophenone, ferulic acid, caffeic acid, glycerol and nitroaniline The matrix material may be combined with additive(s) or analyte(s) prior to or after matrix is deposited on a substrate. When analytes are embedded in a matrix of light-absorbing material, the matrix is generally present in excess relative to the analyte. The incorporation of analyte molecules in some form into the usually crystalline matrix materials during their crystallization, or at least into the boundary surfaces between the small matrix crystals, is advantageous for the MALDI process. In some embodiments, the additive is first mixed with the matrix material in solution, and the combined matrix material/additive solution is deposited on the substrate where it crystallizes.

In various embodiments, matrix is deposited on the substrate to form discrete spots by dissolving the matrix in a solution comprising ascorbic acid and a suitable solvent, such as water. The resulting solution is deposited on the MALDI substrate and the substrate can be placed in a vacuum chamber such that the matrix/ascorbic acid solution is dried under vacuum. In one embodiment, ascorbic acid serves as the matrix material—either alone or in combination with other matrices.

Various methods can be used for depositing the matrix, additive or analyte to a substrate. In one embodiment, the application of each element is done in separate steps. For example, the matrix material can be preloaded on a substrate and the analyte can be added at a later time using an appropriate liquid dispensing apparatus (e.g., piezoelectric, pin tool dispensing devices). In some embodiments, the elements are deposited in combination. For example, the matrix and additive can be first combined (i.e., dissolved in a solvent) and deposited on the substrate together, followed by the addition of an analyte. In some embodiments, a matrix or matrix/additive deposit can be allowed to dry on a substrate, forming crystals of matrix as the solvent evaporates. Subsequent deposition of analyte solution on top of the dried matrix results in partial dissolution of the dried matrix deposit and co-crystallization of the re-dissolved matrix with the analyte.

In certain embodiments, adduct-reducing additive is directly utilized as a matrix material, and in some embodiments, the adduct-reducing additive is utilized as a component of a matrix material. Matrix material in some embodiments includes adduct-reducing additive and one or more of the mass spectrometry matrix materials described herein (e.g., one or more of 3-HPA, DAC, DHB, CHCA, THAP, DCTB, DIT, SA, IAA, HABA). For embodiments in which adduct-reducing additive is utilized with one or more mass spectrometry matrix materials, the adduct-reducing additive ranges between 99% to 1% by weight of the overall weight of the matrix material (e.g., about 5%, 10%, 15%, 20%, 25% 30%, 35%, 40%, 45%, 50%, 55%, 60%, 65%, 70%, 75%, 80%, 85%, 90% or 95% by weight of the overall weight of the matrix material), and sometimes the adduct-reducing additive is in a molar ratio (i.e., moles additive to moles mass spectrometric matrix) of about 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2, for example.

Additive

As used herein, the term "adduct-reducing additive" is a substance added to any one or more of the components or reagents required for analysis by mass spectrometry. These components or reagents include the sample, analyte, matrix material, substrate or combinations thereof. In certain embodiments, the adduct-reducing additive is ascorbic acid, or any derivatives thereof with substantially the same adduct reducing effects.

In certain embodiments, the adduct-reducing additive is a free radical scavenger. Any free radical scavenger suitable for use in mass spectrometric analysis, and in certain instances suitable for use in mass spectrometry analysis of nucleic acids, can be utilized. Examples of free radical scavengers include, without limitation, ascorbic acid, retinol, tocotrienol, tocopherol, coenzyme Q10, melatonin, lycopene, lutein, alpha-carotene, beta-carotene, zeaxanthin, astaxanthin, canthaxanthin, flavones (e.g., luteolin, apigenin, tangeritin), favonols (e.g., quercetin, kaempferol, myricetin, isorhamnetin, proanthocyanidins), favanones (e.g., hasperetin, naringenin, eriodictyol), isoflavone phytoestrogens (e.g., genistein, daidzein, glycitein), stilbenoids (e.g., resveratrol, pterostilbene), anthocyanins (e.g., cyaniding, delphinidin, malvidin, pelargonidin, peonidin, petunidin), phenolic acids and esters (e.g., ellagic acid, gallic acid, salicylic acid, rosmarinic acid, cinnamic acid, chlorogenic acid, chicoric acid, gallotannins, ellagitannins), nonfalvonoid phenolics (e.g., curcumin, xanthones, silymarin, eugenol) and organic antioxidants (e.g., citric acid, oxalic acid, phytic acid, lignan, uric acid, N-acetylcysteine). The person of ordinary skill in the art can readily identify free radical scavengers that are suitable as an additive or matrix for mass spectrometry by routinely testing such scavengers in side-by-side analyses, as shown in the Examples herein.

In some embodiments, the additive is substantially free of impurities and therefore does not need to be purified. If the adduct-reducing additive is not substantially pure, it may be purified by methods known in the art to remove impurities, for example, by ion-exchange resin purification.

The additive can be dissolved in liquid form (e.g., dissolved in water) and then deposited on preloaded matrix or deposited directly on the substrate without preloaded matrix. Alternatively, the additive may be combined with the matrix prior to being deposited on the substrate. The additive and matrix may be combined to obtain a concentration of matrix of 1 to about 20 mg/ml and a concentration of additive from about 5 to about 50 mM. The use of insufficient amounts of additive will not significantly reduce the adduct formation, while using too much additive can suppress the parent signals in the mass spectra. Those of skill in the art are able to determine without undue experimentation the appropriate amount of additive to optimize the analysis of a particular analyte by varying the amount of additive and determining the effect on spectral characteristics.

In some embodiments, the adduct-reducing additive may be used alone or in combination with other substances that reduce or eliminate the presence of unwanted adducts. Ascorbic acid additive can be combined with other additives capable of reducing background noise in mass spectra. Other known, suitable additives include resin, volatile ammonium salts, particularly volatile monobasic, dibasic or tribasic ammonium salts. Preferably the salt additives are not too basic such that they interfere with the sample being analyzed. The additives can be monobasic phosphates and sulfates (e.g., ammonium monobasic phosphate), and dibasic citrates (e.g., ammonium dibasic citrate), and tribasic citrates (e.g., ammonium tribasic citrate).

In certain embodiments, the adduct-reducing additive is ascorbic acid, ascorbate, a salt thereof, a tautomer thereof, or an ascorbic acid analog (including analog salts and tautomers), having a structure according to the following formula:

wherein:

$R^1$ and $R^2$ independently are OH, halogen, $R^3$, $OR^3$, azido, cyano, $CH_2R^3$, $CHR^3R^4$, $SR^3$, $NR^3R^4$; and $R^3$ and $R^4$ independently are H, alkyl, acetylene or cyano, or an optionally substituted aryl carbocyclic ring, aryl heterocyclic ring, non-aryl carbocyclic ring or non-aryl heterocyclic ring. Ascorbic acid analogs used herein generally are free radical scavenging agents, and free radical scavenging activity of an ascorbic acid analog can be determined by the person of ordinary skill in the art (e.g., titration with an oxidation agent such as 2,6-dichlorophenol-indophenol (DCPIP), iodine, iodate and iodide mixture or N-bromosuccinimide).

The term "optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

Ascorbic acid and analogs thereof can have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge.

Ascorbic acid analogs often contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed. The compounds of the invention may also exist in more than one tautomeric form; the depiction herein of one tautomer is for convenience only, and is also understood to encompass other tautomers of the form shown.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2 propenyl, 3 butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described.

Typically, the alkyl, alkenyl and alkynyl substituents of the invention contain one 10C (alkyl) or two 10C (alkenyl or alkynyl). Preferably they contain one 8C (alkyl) or two 8C (alkenyl or alkynyl). Sometimes they contain one 4C (alkyl) or two 4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often optionally substituted to the extent that such substitution makes sense chemically. Typical substituents include, but are not limited to, halo, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" substituents are 2-10C alkynyl groups that are optionally substituted, and are of the formula —C≡C—Ra, wherein Ra is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each Ra group is optionally substituted with one or more substituents selected from halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and wherein two R' can be linked to form a 3-7 membered ring optionally containing up to three heteroatoms selected from N, O and S. In some embodiments, Ra of —C≡C—Ra is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one to three O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5 membered rings as well as 6 membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR2, SR, SO2R, SO2NR2, NRSO2R, NRCONR2, NRCOOR, NRCOR, CN, COOR, CONR2, OOCR, COR, and NO2, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R7 is alkyl, this alkyl may optionally be substituted by the remaining substituents listed as embodiments for R7 where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", as used herein includes fluoro, chloro, bromo and iodo. Fluoro and chloro are often preferred. "Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle" refers to a cyclic compound containing only carbon atoms in the ring, whereas a "heterocycle" refers to a cyclic compound comprising a heteroatom.

The carbocyclic and heterocyclic structures encompass compounds having monocyclic, bicyclic or multiple ring systems. As used herein, the term "heteroatom" refers to any atom that is not carbon or hydrogen, such as nitrogen, oxygen or sulfur. Illustrative examples of heterocycles include but are not limited to tetrahydrofuran, 1,3 dioxolane, 2,3 dihydrofuran, pyran, tetrahydropyran, benzofuran, isobenzofuran, 1,3 dihydro isobenzofuran, isoxazole, 4,5 dihydroisoxazole, piperidine, pyrrolidine, pyrrolidin 2 one, pyrrole, pyridine, pyrimidine, octahydro pyrrolo[3,4 b]pyridine, piperazine, pyrazine, morpholine, thiomorpholine, imidazole, imidazolidine 2,4 dione, 1,3 dihydrobenzimidazol 2 one, indole, thiazole, benzothiazole, thiadiazole, thiophene, tetrahydro thiophene 1,1 dioxide, diazepine, triazole, guanidine, diazabicyclo [2.2.1]heptane, 2,5 diazabicyclo[2.2.1]heptane, 2,3,4,4a,9,9a hexahydro 1H beta carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

Substrate

As used herein, "substrate" refers to an insoluble support on which an analyte is deposited and analyzed. Substrates may include, but are not limited to, silica, glass (e.g. glass, controlled-pore glass (CPG)), nylon, Wang resin, Merrifield resin, Sephadex, Sepharose, cellulose, magnetic beads, Dynabeads, a metal surface (e.g. steel, gold, silver, aluminum, silicon and copper), a plastic material (e.g., polyethylene, polypropylene, polyamide, polyester, polyvinylidenedifluoride (PVDF)), or pins (e.g., arrays of pins suitable for combinatorial synthesis or analysis or beads in pits of flat surfaces such as wafers (e.g., silicon wafers) with or without plates. The solid support may be in any desired form, including, but not limited to: a bead, chip, capillary, plate, membrane, wafer, comb, pin, a wafer with pits, substantially flat surface, an array of pits or nanoliter wells and other geometries and forms known to those of skill in the art. Preferred supports are flat surfaces designed to receive or link samples at discrete loci. Most preferred are flat surfaces with hydrophobic regions surrounding hydrophilic loci for receiving, containing or binding a sample. The substrate materials can be inert to the operation of the device or the reagents to be used in the procedure, including the matrix materials and solvents typical of MALDI mass spectrometry.

On the substrate, spots of matrix or matrix/additive or matrix/analyte/additive often have certain characteristics. Each spot on a substrate can be about 200 micrometers to about 1 mm in diameter. Spot diameter often is substantially uniform and spot-to-spot diameter variation often is minimal (e.g., variation of about 20 micrometers). Any center-to-center distance for spots on a substrate useful for mass spectrometry can be utilized, such as center-to-center distances of 2.25 mm or 1.125 mm, for example, and the center-to-center distance between spots on a substrate often is substantially uniform. Spots on the substrate can have a thickness ranging between about 10 micrometers to about 100 micrometers. The thickness of each spot on a substrate often is substantially uniform and spot-to-spot thickness variation often is minimal (e.g., about 30 micrometers).

Target Site

As used herein, the term "target site" refers to a specific locus on a substrate upon which material, such as matrix material, matrix material with additive, or analyte, can be deposited and retained. A substrate may contain one or more target sites, which can be arranged randomly or in ordered array or other pattern. When used for mass spectrometric analyses, such as MALDI analyses, a target site or the resulting site with deposited material, is preferably equal to or less than the size of the laser spot that will be focused on the substrate to effect desorption. Thus, a target site can be, for example, a well or pit, a pin or bead, or a physical barrier that is positioned on a surface of the solid support, or combinations thereof such as a beads on a chip, chips in wells, or the like. A target site can be physically placed onto the substrate, can be etched on a surface of the substrate, can be a "tower" that remains following etching around a locus, or can be defined by physical-chemical parameters such as relative hydrophilicity, hydrophobicity, or any other surface chemistry that retains a liquid therein or thereon.

Platform

The methods and compositions of the present invention may be used in conjunction with any ionization source, including Atmospheric Pressure, Chemical Ionisation (APCI), Chemical Ionisation (CI), Electron Impact (EI), Electrospray Ionisation (ESI or ES), Fast Atom Bombardment (FAB), Field Desorption/Field Ionisation (FD/FI), Matrix Assisted Laser Desorption Ionisation (MALDI) and Thermospray Ionisation (TSP). In certain embodiments, the ionization source is MALDI or ES.

The methods and compositions of the invention may be used in conjunction with any mass analyzer. There are a number of mass analyzers currently available, the better known of which include quadrupoles, time-of-flight (TOF) analyzers, magnetic sectors, and both Fourier transform and quadrupole ion traps. In addition, the analyzers may be used in tandem as tandem (MS-MS) mass spectrometers. In some embodiments the mass analyzer is a TOF analyzer.

EXAMPLES

The following examples are non-limiting and illustrate certain embodiments of the invention.

Example 1

Additive to the Analyte

In the following Example, analyte from a Sequenom iPLEX™ reaction was mixed with either nanopure water or with an ascorbic acid additive to determine the effect of the additive on adduct formation. The plates were processed in parallel following the Sequenom iPLEX™ protocol as described by Jurinke, C., Oeth, P., van den Boom, D., MALDI-TOF mass spectrometry: a versatile tool for high-performance DNA analysis. *Mol. Biotechnol.* 26, 147-164 (2004); and Oeth, P. et al., iPLEX™ Assay: Increased Plexing Efficiency and Flexibility for MassARRAY® System through single base primer extension with mass-modified Terminators. SEQUENOM Application Note (2005), both of which are hereby incorporated by reference. During the dilution/conditioning step, 9 □l of analyte solution was mixed with 25 □l of nanopure water as the standard protocol dictates, while the other plate was also mixed with ascorbic acid to yield a final ascorbic acid concentration of 20 mM.

To remove residual cations from the ascorbic acid, and to exclude any possible inference from ammoniated cation exchange resin, stock solutions of ascorbic acid were desalted with 1 g/ml of protonated resin. Depending on the workflow, the additive can be either mixed directly with the analyte or further diluted and then added to the sample. In this particular Example, the dilution step was completed on an automated liquid handler, with the dilution solution stored in a 50 ml tray at a volume ratio of 1/25 prior to its addition to the analyte solution.

Following the respective dilution/conditioning steps, both plates were dispensed at 10 nl/domain to a pre-matrixed standard SpectroChip™ (300 mM 3-HPA/25 mMDAC) using a Sequenom Nanodispenser, and analyzed on a Sequenom MassARRAY® Analyzer Compact.

Results: the use of ascorbic acid led to an 8% higher number of calls for ascorbic acid-treated samples. Sodium and ammonia adducts were suppressed to the detection limit in the ascorbic acid treated samples. This resulted in no false positive calls due to ammonia and/or sodium adducts for the ascorbic acid treated samples, while ammonia adducts in water conditioned samples caused one assay to be repeatedly assigned heterozygote (a false positive call).

Example 2

Additive to the Matrix

In the following Example, a new matrix composition comprising ascorbic acid (AA) was shown to reduce adduct formation, thereby improving spectrum quality.

Matrix Solutions

Matrix combinations were prepared from the following stock solutions and nanopure water (stock solutions of the different matrix components were treated with cation exchange resin according to the components' functional group—acids with exchange resin in H+ form, and ammonia salts with resin in NH4+ form):

3-HPA: 350 mM in 30% aqueous Acetonitrile.

AA: 1M in aqueous solution.

DAC: 226 mg 1 Min aqueous solution.

The standard matrix was prepared with 300 mM 3HPA and 25 mM DAC, while the new matrix was prepared with 300 mM 3HPA, 20 mM $NH_4$-Oxalate and 20 mM ascorbic acid. See Table 1. The final matrices were dispensed on a Spectro-Chip at 15-20 nl, using a Gesim Nanoplotter.

TABLE 1

| Matrix Type | Matrix Composition (concentrations in [mM]) |
|---|---|
| Standard, no resin | 300 HPA/25 DAC |
| Standard, with resin | 300 HPA/25 DAC |
| new Matrix | 300 HPA/20 AA/20 NH4-Oxalate |

Synthetic Oligonucleotide Samples

Figure 2:
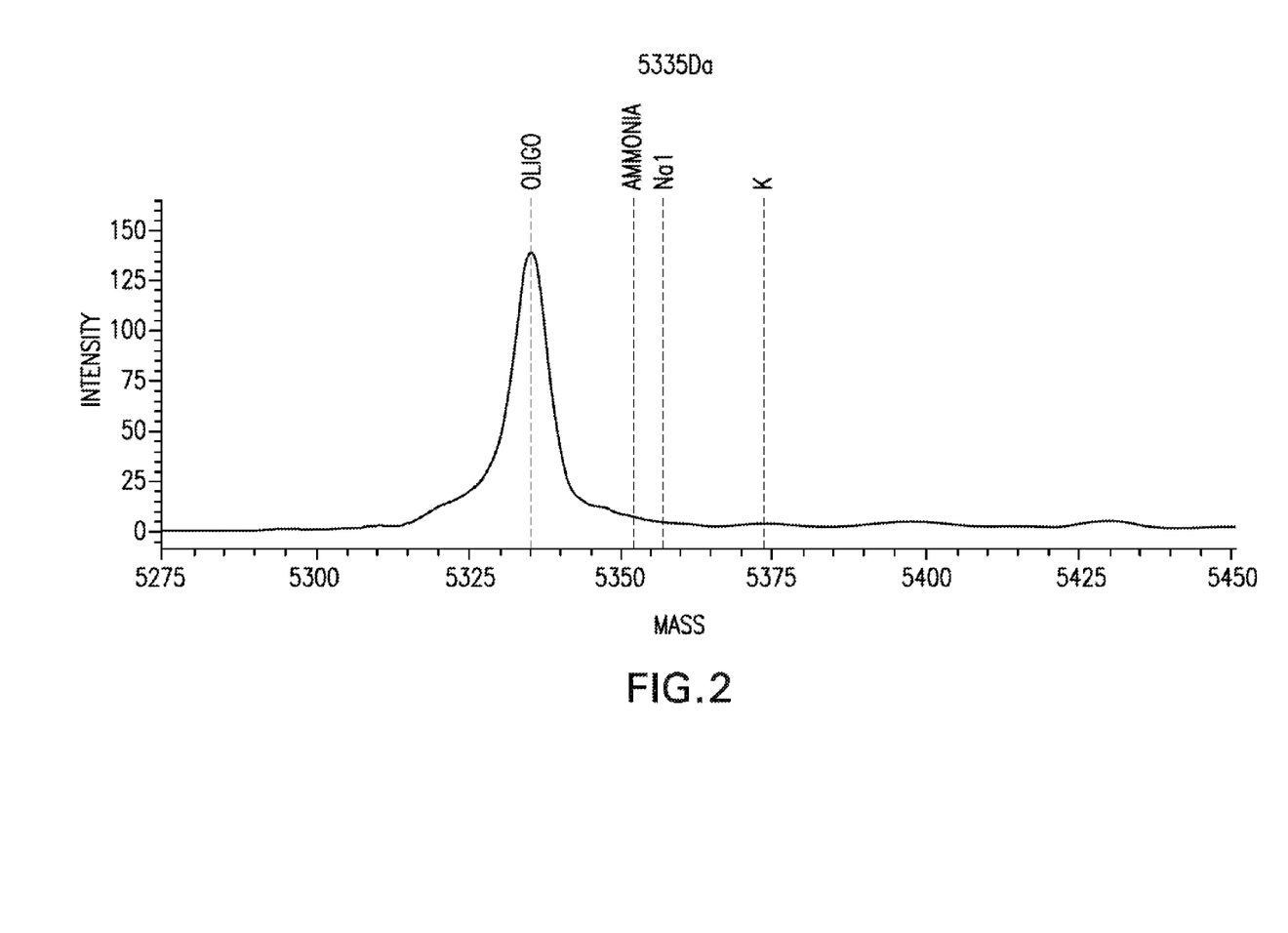
FIG. 2 shows a mass spectrum generated using the same 17mer synthetic oligonucleotide (GTG GTG GTG GTG GTG GT (SEQ ID NO: 1)) spotted directly on the ascorbic acid-modified matrix. As seen in the Figure, the ammonia adduct is no longer present.

Two experiments were performed using synthetic oligonucleotides spotted directly on the matrices of Table 1. In a first experiment, a 17mer synthetic oligonucleotide (GTG GTG GTG GTG GTG GT (SEQ ID NO: 1)) was tested on both the "old", resin-treated matrix and the "new", ascorbic acid-modified matrix. In FIG. 1 (old matrix), an ammonia adduct is clearly present (peak height is approximately 12% of parent peak at 5335 Da), while the ammonia adduct is not present in FIG. 2 (new matrix). The new matrix may alternatively be referred to as "Matrix 63C".

In a second experiment, a low mass 17mer synthetic oligonucleotide (5044 Da) and high mass 28mer synthetic oligonucleotide (8436 Da) were tested for adduct formation and depurination.

In both experiments, the synthetic oligonucleotide analytes were dispensed on the matrices of Table 1 at 10 nl per spot, using a Gesim nanoplotter. The results for the low mass and high mass oligonucleotides are shown in Tables 2 and 3, respectively.

TABLE 2A

17mer Adducts

| Adducts to 17mer, 5044 Da sample size: 48 | Standard Matrix, not resin treated | Standard Matrix, resin treated | new Matrix |
|---|---|---|---|
| NH3 (+17 Da) | 0.4 * 2.3 = 0.9<br>3% | 0 | 0 |
| HPA (+138 Da) | 0.17 * 1.8 = 0.3<br>3% | 0 | 0 |
| HPA Decarboxylated 1 (+94 Da) | 0.48 * 2.4 = 1.2<br>4% | 0 | 0.13 * 1.6 = 0.2<br>2% |
| HPA Decarboxylated 2 (+188 Da) | 0.98 * 5 = 4.9<br>7% | 1 * 10.2 = 10.2<br>9% | 1 * 8.9 = 8.9<br>11% |
| Potassium (+38 Da) | 0.46 * 2.5 = 1.2<br>4% | 0 | 0 |
| Sodium (+22 Da) | 0.52 * 3.4 = 1.8<br>5% | 0 | 0 |
| Carbonic Acid (+62 Da) | 0.08 * 1.4 = 0.1<br>2% | 0 | 0.06 * 1.3 = 0.08<br>2% |
| Average adduct formation score | 1.5 | 1.5 | 1.3 |
| Depurination | 0 | 0 | 0 |

TABLE 2B

17mer Probe Height and Signal-to-Noise (SNR) Ratio

| Probe | Standard Matrix, not resin treated | Standard Matrix, resin treated | new Matrix |
|---|---|---|---|
| Probe Height (avg./stdev.) | 69/19 | 110/24 | 79/26 |
| Probe SNR (avg./stdev.) | 241/57 | 388/71 | 313/77 |

TABLE 3A

28mer Adducts

| Adducts to 28mer, 8436 Da sample size: 48 | Standard Matrix, not resin treated | Standard Matrix, resin treated | new Matrix |
|---|---|---|---|
| NH3 (+17 Da) | 1 * 3.8 = 3.8<br>19% | 1 * 3.9 = 3.9<br>14% | 0.46 * 2.1 = 1<br>7% |
| HPA (+138 Da) | 0.35 * 1.2 = 0.42<br>6% | 0.6 * 1.6 = 1<br>6% | 0.67 * 1.1 = 0.74<br>4% |
| HPA Decarboxylated 1 (+94 Da) | 0.35 * 1.3 = 0.46<br>7% | 0.6 * 1.7 = 1<br>6% | 0.46 * 1.7 = 0.78<br>6% |
| HPA Decarboxylated 2 (+188 Da) | 0.35 * 1.3 = 0.46<br>7% | 0.65 * 2.6 = 1.7<br>9% | 1 * 3.5 = 3.5<br>11% |
| Potassium (+38 Da) | 0.39 * 1.3 = 0.5<br>7% | 0.58 * 1 = 0.58<br>4% | 0.4 * 0.9 = 0.36<br>3% |
| Sodium (+22 Da) | 0.46 * 2.4 = 1.1<br>12% | 0.6 * 1.8 = 1.1<br>6% | 0.46 * 1.1 = 0.51<br>4% |
| Carbonic Acid (+62 Da) | 0.31 * 0.8 = 0.2<br>4% | 0.31 * 0.8 = 0.2<br>3% | 0.17 * 0.8 = 0.14<br>3% |
| Average adduct formation score | 1 | 1.4 | 1 |
| Depurination score: | | | |
| substitution G: −133 Da | 0.29 * 0.6 = 0.2 | 0.46 * 0.8 = 0.4 | 0.46 * 1.2 = 0.6 |
| elimination G: −150 Da | 0 | 0 | 0 |
| substitution A: −117 Da | 0 | 0 | 0 |

TABLE 3B

28mer Probe Height and Signal-to-Noise (SNR) Ratio

| Probe | | | |
|---|---|---|---|
| Probe Height (avg./stdev.) | 20/5 | 28/7 | 31/7 |
| Probe SNR (avg./stdev.) | 93/19 | 134/27 | 164/31 |

Matrix comparisons are based on the relative adduct and depurination peak heights, and on the probe heights and SNRs. An adduct formation score was introduced to account for the relative frequency of pads that exceed the peak score threshold value into the analysis:

Adduct formation score=(relative frequency of pads exceeding threshold value)*(average adduct peak height)

The term "pads" and "spots" on a substrate are interchangeable. Standard deviations for the average adduct peak heights were low and comparable for all matrices and are not reported in the tables.

For the synthetic 17mer, the average adduct formation score was 13% less on the new matrix (Table 2A), and for the synthetic 28mer, the average adduct formation score was 29% less on the new matrix (Table 3A) as compared to the resin-treated standard matrix.

Primer Extension Samples

Additional experiments were performed using validated Sequenom genotyping assays directed to polymorphisms in the RhD and AMG genes. These assays were performed using the iPLEX™ assay and MassARRAY® technology (Jurinke, C., Oeth, P., van den Boom, D., MALDI-TOF mass spectrometry: a versatile tool for high-performance DNA analysis. Mol. Biotechnol. 26, 147-164 (2004); and Oeth, P. et al., iPLEX™ Assay: Increased Plexing Efficiency and Flexibility for MassARRAY® System through single base primer extension with mass-modified Terminators. SEQUENOM Application Note (2005), both of which are hereby incorporated by reference). In brief, the target region surrounding the SNP is first amplified by PCR. Subsequently an oligonucleotide primer is annealed to the PCR product and is extended allele-specifically by a single nucleotide using a mixture of 4 terminator nucleotides and a DNA polymerase. The extension products are transferred to a miniaturized chip array and are analyzed by MALDI-TOF Mass Spectrometry. Determination of the molecular mass of extension products allows unambiguous identification of the SNP allele present in the sample. The peak area ratio of mass signals allows the estimation of the relative abundance of the alleles in a given sample. In this experiment, a 20% higher laser energy (compared to the above synthetic oligonucleotide experiments) was used on 7316 Da AMG primer extension products spotted on the matrices of Table 1. As Tables 4 and 5 shows, there is a reduced average adduct formation score for the extension products dispensed on the new matrix as compared to the standard matrix (40-50% decrease), and the increased laser energy had no negative effect on adduct formation.

TABLE 4A

AMG Assay (7316 Da) Adducts - Standard Laser Energy

| Fetal Quantifier Adducts to probe at 7316 Da sample size: 96 | Standard Matrix, not resin treated | Standard Matrix, resin treated | new Matrix |
|---|---|---|---|
| NH3 (+17 Da) | 1 * 2.5 = 2.5 <br> 16% | 1 * 2.1 = 2.1 <br> 11% | 0.94 * 1 = 0.94 <br> 6% |
| Sodium (+22 Da) | 0.91 * 1.7 = 1.5 <br> 11% | 0.98 * 0.9 = 0.9 <br> 5% | 0.25 * 0.5 = 0.13 <br> 3% |
| Potassium (+38 Da) | 0.9 * 1.2 = 1.1 <br> 8% | 0.96 * 1.1 = 1.1 <br> 6% | 0.89 * 0.8 = 0.7 <br> 4% |
| Carbonic Acid (+62 Da) | 0.9 * 1.2 = 1.1 <br> 8% | 0.98 * 1.3 = 1.3 <br> 7% | 0.98 * 1.4 = 1.4 <br> 8% |
| Average adduct formation score | 1.6 | 1.4 | 0.8 |

TABLE 4B

AMG Assay (7316 Da) Height and Signal-to-Noise (SNR) Ratio

| Probe | | | |
|---|---|---|---|
| Probe Height (avg./stdev.) | 16/4 | 19/5 | 18/6 |
| Probe SNR (avg./stdev.) | 54/11 | 65/14 | 66/19 |

TABLE 5

AMG Assay (7316 Da) Adducts - Increased Laser Energy

| Fetal Quantifier Adducts to probe at 7316 Da sample size: 96 | Standard Matrix, resin treated 20% increased laser energy | new Matrix 20% increased laser energy |
|---|---|---|
| NH3 (+17 Da) | 1 * 1.7 = 1.7 <br> 11% | 0.55 * 0.85 = 0.47 <br> 5% |
| Sodium (+22 Da) | 0.98 * 1.1 = 1.1 <br> 7% | 0.06 * 0.51 = 0.03 <br> 3% |
| Potassium (+38 Da) | 0.1 * 0.4 = 0.04 <br> 0.3% | 0.41 * 0.75 = 0.31 <br> 3% |
| Carbonic Acid (+62 Da) | 0.98 * 1.5 = 1.5 <br> 9% | 0.97 * 1.6 = 1.6 <br> 8% |
| Average adduct formation score | 1.1 | 0.6 |
| Probe | | |
| Probe Height (avg./stdev.) | 16/4 | 19/4 |
| Probe SNR (avg./stdev.) | 65/14 | 69/13 |

To test the new matrix's effectiveness in the presence of higher amounts of analyte, increasing amounts (10μ, 15 and 20 nl) of 7528 Da AMG primer extension products were analyzed on the matrices of Table 1. See Table 6 below. The new matrix's average adduct formation scores are lower at the 10 and 15 nl analyte volume; whereas at 20 nl, the same score (0.6) was observed for both matrices.

TABLE 6

AMG Assay (7528 Da) Adducts - Increased Analyte Sample on the Matrix

Fetal Quantifier Adducts to probe at 7528Da sample size: 24

| | Standard Matrix, resin treated | | | new Matrix | | |
|---|---|---|---|---|---|---|
| | \multicolumn{6}{c}{Probe volume [nl]} | | | | | |
| | 10 | 15 | 20 | 10 | 15 | 20 |
| NH3 (+17Da) | 0.92 * 1.3 = 1.2  8% | 0.92 * 0.8 = 0.73  8% | 0.92 * 0.6 = 0.55  10% | 0.96 * 0.9 = 0.86  4% | 0.88 * 0.6 = 0.53  4% | 0.88 * 0.3 = 0.26  4% |
| Sodium (+22Da) | 0.92 * 1 = 0.92  6% | 0.92 * 0.7 = 0.64  7% | 0.92 * 0.6 = 0.55  10% | 0 | 0.21 * 0.3 = 0.06  2% | 0.5 * 0.3 = 0.15  4% |
| Potassium (+38Da) | 0.67 * 0.8 = 0.5  5% | 0.92 * 0.7 = 0.64  7% | 0.92 * 0.7 = 0.64  12% | 0.83 * 1.2 = 1  6% | 1 * 1.1 = 1.1  7% | 1 * 1.2 = 1.2  15% |
| Carbonic Acid (+62Da) | 1 * 1.6 = 1.6  10% | 1 * 1.2 = 1.2  12% | 0.92 * 0.7 = 0.64  12% | 1 * 1.9 = 1.9  9% | 0.96 * 1.3 = 1.25  9% | 1 * 0.8 = 0.8  10% |
| Average adduct formation score Probe | 1.1 | 0.8 | 0.6 | 0.9 | 0.7 | 0.6 |
| Probe Height (avg./stdev.) | 16/4 | 10/3 | 6/3 | 21/5 | 15/5 | 8/3 |
| Probe SNR (avg./stdev.) | 85/19 | 56/17 | 30/14 | 103/21 | 68/22 | 37/10 |
| Relative SNR reduction | 34% | 46% | | 34% | 46% | |

Improved Mass Spectra

Figure 3:
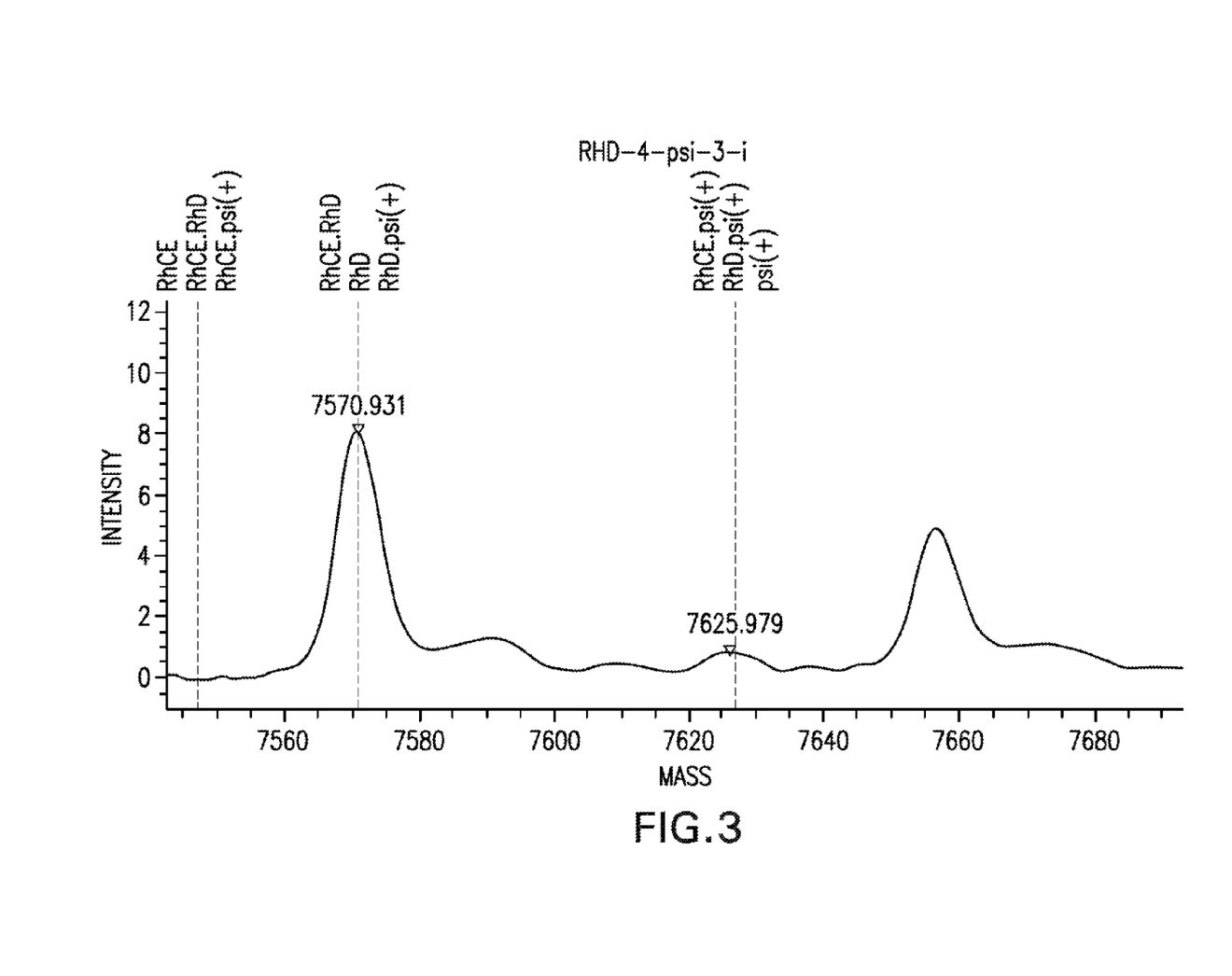
FIG. 3 shows a mass spectrum generated from an RhD gene extension product spotted on a standard, unmodified matrix resulting in an extension peak at 7571 Da and a +55 Da adduct peak (NH3+K) at 7626 Da. The adduct peak causes a false positive insertion call (SNR: 2; Probability: 88%).
Figure 4:
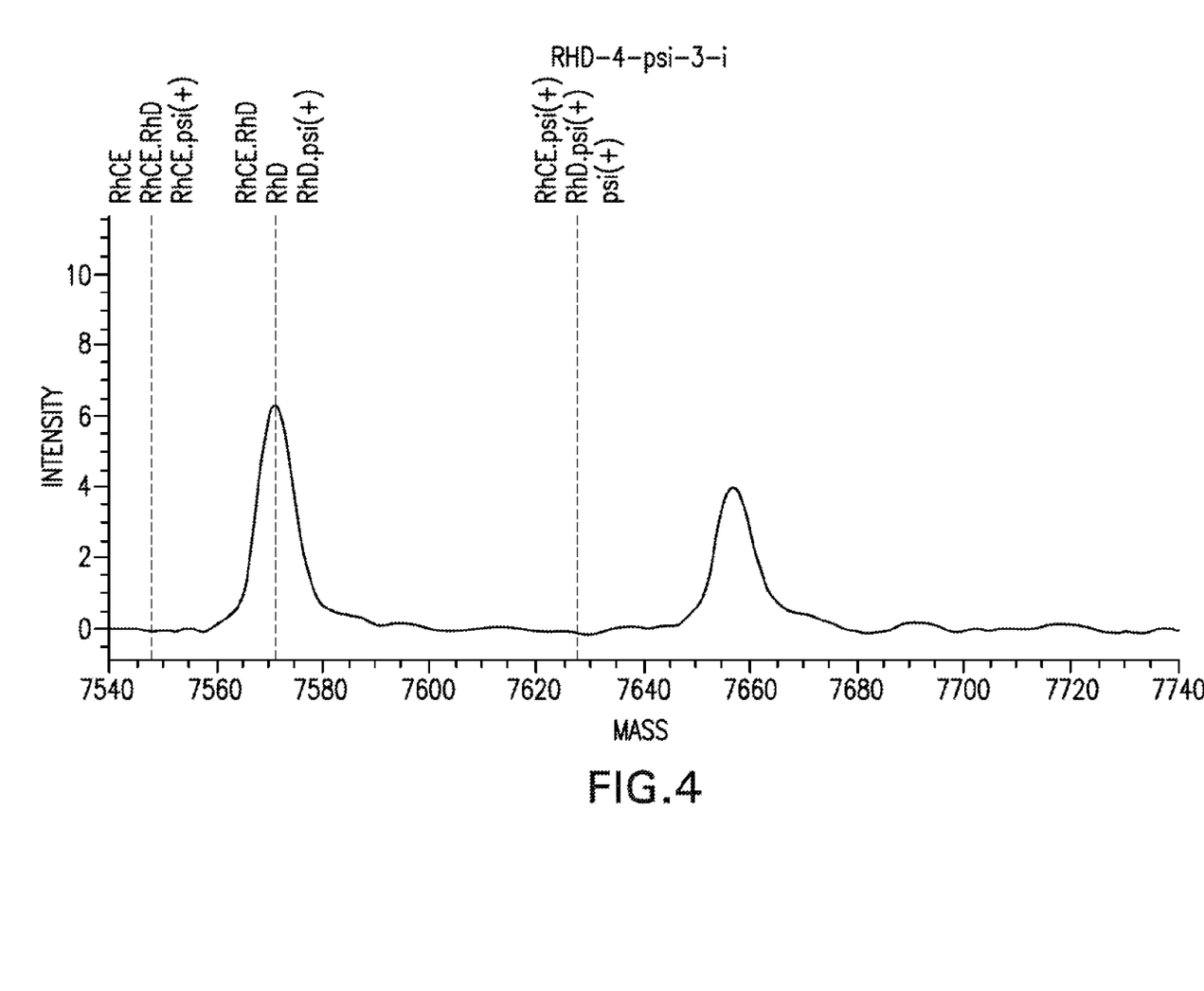
FIG. 4 shows a mass spectrum generated from an RhD gene extension product spotted on the ascorbic-acid modified matrix resulting in an extension peak at 7571 Da, but no +55 Da adduct peak. The false positive insertion call is eliminated (SNR: 0; Probability: 0%).

The importance of reduced adduct formation to eliminate false positive calls is clearly illustrated in FIGS. 3 and 4, which show the results for the RHD-4-psi 3-i genotyping assay. The peak at 7626 Da is not an insertion as reported for the standard matrix (FIG. 3), but a 55 Da ($NH_3$+K) adduct to the extension product at 7571 Da. This adduct is clearly eliminated in the new matrix (FIG. 4).

Example 3

Additive to the Matrix and Analyte

The new, ascorbic acid-modified matrix was also tested in combination with ascorbic acid added to an analyte solution (AMG primer extension product at 8289 Da). As seen in Example 1 and Tables 2-6 of Example 2, ascorbic acid added to the analyte or in combination with standard matrix greatly reduced ammonia and sodium adducts. See Table 7 below. There was a 43% decrease for ascorbic acid treated analyte on standard matrix, and a 57% decrease for ascorbic acid treated analyte dispensed on new matrix (as compared to untreated analyte dispensed on untreated matrix).

TABLE 7

Ascorbic Acid Added to Analyte and Matrix

| Fetal Quantifier Adducts to probe at 8289 Da sample size: 24 | Standard Matrix, resin treated | Standard Matrix, resin treated | new Matrix | new Matrix |
|---|---|---|---|---|
| Final suppressant concentration in analyte | 0 | 20 mM | 0 | 20 mM |
| NH3 (+17Da) | 1 * 1.4 = 1.4  18% | 1 * 0.6 = 0.6  10% | 1 * 0.6 = 0.6  8% | 0.92 * 0.5 = 0.46  8% |
| Sodium (+22Da) | 0.96 * 0.7 = 0.67  9% | 0.63 * 0.3 = 0.19  5% | 0.17 * 0.3 = 0.05  4% | 0.29 * 0.1 = 0.03  2% |
| Potassium (+38Da) | 0.21 * 0.3 = 0.06  4% | 0.13 * 0.1 = 0.01  2% | 0.17 * 0.2 = 0.03  3% | 0.17 * 0.2 = 0.03  3% |
| Carbonic Acid (+62Da) | 0.96 * 0.8 = 0.77  10% | 1 * 0.7 = 0.7  12% | 1 * 0.9 = 0.9  11% | 0.96 * 0.8 = 0.77  13% |
| Average adduct formation score Probe | 0.7 | 0.4 (43%) | 0.4 | 0.3 (25%) |
| Probe Height (avg./stdev.) | 8/2.3 | 6/3 | 8/3 | 6/2 |
| Probe SNR (avg./stdev.) | 35/8 | 32/11 | 36/12 | 30/7 |

Example 4

Stability Tests

Over a period of six months, four stability tests were performed to determine the adduct-reducing properties of ascorbic acid over time. There was no indication that the tested matrices diminish in their performance during the course of time. Instead, the obtained SNRs and consistent adduct formation scores for ammonia and alkali adducts confirmed the stability of 3-HPA and its additives DAC, $NH_4$-Oxalate in combination with ascorbic acid.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a device" can mean one or more devices) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claims that follow.

---

---

What is claimed is:

1. A method of mass spectrometric analysis, comprising:
   (a) providing a composition comprising an analyte and an additive that includes ascorbic acid, or a salt, tautomer or analog thereof, and
   (b) analyzing the analyte by mass spectrometry, wherein the additive in the composition is in an amount that reduces the amount of an adduct formed under mass spectrometry conditions.

2. The method of claim 1, wherein the additive consists essentially of ascorbic acid, or a salt, tautomer or analog thereof.

3. The method of claim 1, wherein the additive consists of ascorbic acid, or a salt, tautomer or analog thereof.

4. The method of claim 1, wherein the additive consists essentially of ascorbic acid.

5. The method of claim 1, wherein the additive consists of ascorbic acid.

6. The method of claim 1, wherein the additive further comprises ammonium oxalate.

7. The method of claim 1, wherein the analyte is a nucleic acid.

8. The method of claim 7, wherein the nucleic acid is deoxyribonucleic acid.

9. The method of claim 7, wherein the nucleic acid is ribonucleic acid.

10. The method of claim 1, wherein the mass spectrometry is selected from the group consisting of: Matrix-Assisted Laser Desorption/Ionization Time-of-Flight (MALDI-TOF) Mass Spectrometry, Laser Desorption Mass Spectrometry (LDMS), Electrospray (ES) Mass Spectrometry, Ion Cyclotron Resonance (ICR) Mass Spectrometry, and Fourier Transform Mass Spectrometry.

11. The method of claim 1, wherein the composition comprises 5 mM to 50 mM ascorbic acid, or a salt, tautomer or analog thereof.

12. The method of claim 1, wherein the composition comprises a mass spectrometry matrix.

13. The method of claim 12, wherein the mass spectrometry matrix comprises 3-hydroxy picolinic acid (3-HPA).

14. The method of claim 12, wherein the mass spectrometry matrix comprises di-ammonium citrate (DAC).

* * * * *

SEQUENCE LISTING

<160> NUMBER OF SEQ ID NOS: 1

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtggtggtgg tggtggt                                                  17